United States Patent [19]

Chen et al.

[11] Patent Number: 5,218,125
[45] Date of Patent: Jun. 8, 1993

[54] ANTIHYPERTENSIVE COMPOUND AND METHOD OF USE THEREAS

[75] Inventors: Shieh-Shung T. Chen, Morgansville; Lydia T. So, Maywood; Raymond F. White, Englishtown, all of N.J.

[73] Assignee: Merck & Co., Inc., Rahway, N.J.

[21] Appl. No.: 873,433

[22] Filed: Apr. 23, 1992

[51] Int. Cl.$^5$ .................. C07D 405/01; A61K 31/41
[52] U.S. Cl. ...................... 548/252; 514/301
[58] Field of Search ................ 548/252; 514/381

[56] References Cited

FOREIGN PATENT DOCUMENTS

0253310A2 9/1987 European Pat. Off. .

OTHER PUBLICATIONS

Ralph A. Stearns et al., Drug Metabolism and Disposition, Vol. 20, No. 2, pp. 281–287 (1992).

*Primary Examiner*—David B. Springer
*Attorney, Agent, or Firm*—William H. Nicholson; Joseph F. DiPrima; Christine E. Carty

[57] ABSTRACT

Fermentation of the microorganism Streptomyces sp. MA6966 (ATCC 55293) in the presence of the Angiotensin II (A II) receptor antagonist

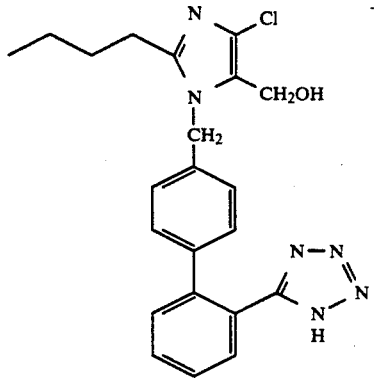

yields a new compound hydroxylated in the 2-butyl group which is also an A II antagonist useful in the treatment of hypertension and congestive heart failure and other indications known to respond to A II antagonists.

3 Claims, No Drawings

ANTIHYPERTENSIVE COMPOUND AND METHOD OF USE THEREAS

BACKGROUND OF THE INVENTION

This invention relates to a novel process for the preparation of the antihypertensive agent, compound (I)

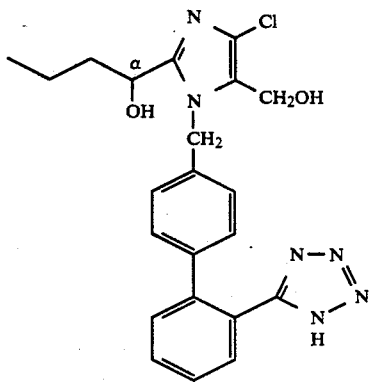

comprising fermentation of compound (II)

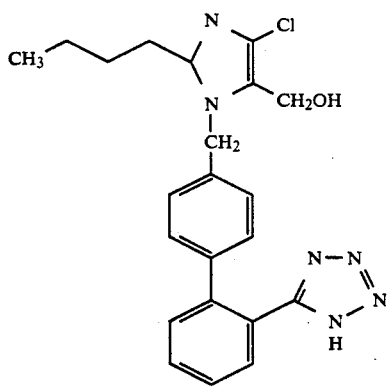

with the microorganism Streptomyces sp. MA6966 (ATCC 55293) or a mutant thereof. Compound (I) and its precursor (II) are Angiotensin II (A II) receptor antagonists useful in the treatment of human hypertensive diseases.

A II is an octapeptide hormone produced mainly in the blood during the cleavage of Angiotensin I by angiotensin converting enzyme (ACE). ACE is localized on the endothelium of blood vessels of lung, kidney and many other organs. A II is the end product of the renin-angiotensin system (RAS), a system that plays a central role in the regulation of normal blood pressure and seems to be critically involved in hypertension development and maintenance, as well as congestive heart failure. A II is a powerful arterial vasoconstrictor that exerts its action by interacting with specific receptors present on cell membranes. A II receptor antagonism is one of the possible modes of controlling the RAS.

SUMMARY OF THE INVENTION

A new antihypertensive biotransformation product (I) is obtained by the fermentation of the microorganism Streptomyces sp. MA6696 or a mutant thereof, (ATCC 55293) in the presence of substrate compound (II). The biotransformation is accomplished under submerged aerobic conditions in an aqueous carbohydrate medium containing a nitrogen nutrient at a pH of about 7 for a sufficient time to produce compound (I).

The resultant analog exhibits A II antagonist activity, i.e., it has an inhibitory concentration ($IC_{50}$) of less than 50 $\mu$M in an assay that measures the concentration of potential A II antagonist needed to achieve 50% displacement of the total $^{125}$I-Sar$^1$Ile$^8$-angiotensin II specifically bound to a membrane preparation derived from rabbit aortae, and therefore they are antihypertensive agents. This assay is also referred to herein as the "$IC_{50}$" assay.

Also provided by this invention is a pharmaceutical composition containing a therapeutically effective amount of compound (I) in combination with a pharmaceutically acceptable non-toxic carrier or excipient.

In addition, there is provided a method of treating a human host to control hypertensive disorders or for treating congestive heart failure comprising administering to the host a therapeutically effective amount of compound (I).

DETAILED DESCRIPTION OF THE INVENTION

The product of this invention is compound (I)

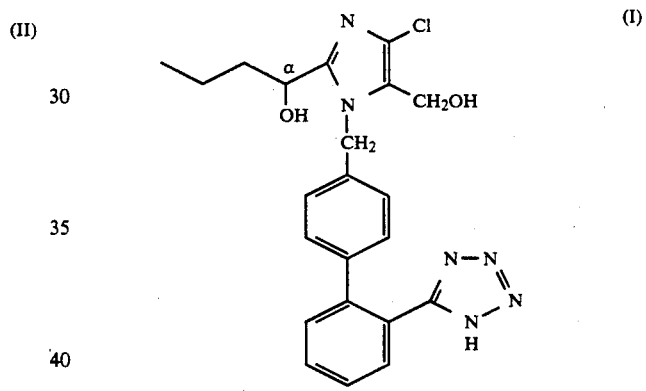

The novel process of this invention comprises fermentation of the microorganism Streptomyces sp. MA6966 (ATCC 55293) or a mutant thereof in the presence of substrate compound (II)

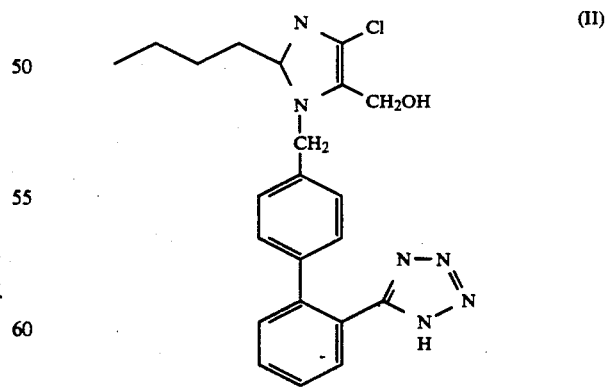

in a nutrient medium, and isolation of the resulting biotransformation product, compound (I) in a conventional manner.

A biologically pure culture of Streptomyces sp. MA6966 has been deposited in the permanent culture collection of the American Type Culture Collection, 12301 Parklawn Drive, Rockville, Md., and is available under the Accession Number ATCC 55293. Mutants of Streptomyces sp. MA6966 are prepared by convential procedures.

In general, compound (I) can be produced by culturing the above-described microorganism in the presence of an appropriate concentration of substrate compound (II) in an aqueous nutrient medium containing sources of assimilable carbon and nitrogen, preferably under submerged aerobic conditions (e.g. shaking culture, submerged culture).

Compound (II) may be prepared according to the procedures described in European Patent Application 0253310 A2. An appropriate concentration of the substrate compound in the aqueous medium ranges from 0.05 mg/mL to 0.2 mg/mL, preferably 0.05 mg/mL; less than 0.05 mg/mL is inefficient and greater than 0.2 mg/ml can inhibit the culture.

The aqueous medium is incubated at a temperature between 26° C. and 29° C., preferably 27° C.; culture growth will be inhibited below this temperature range and culture death will occur above this temperature range. The aqueous medium is incubated for a period of time necessary to complete the biotransformation as monitored by high performance liquid chromatography (HPLC), usually for a period of about 4 days, on a rotary shaker operating at about 220 rpm with a throw of about 2 inches. The aqueous medium is maintained at a pH between 6 and 8, preferably about 7, at the initiation and termination (harvest) of the fermentation process. A higher or lower pH will be detrimental to the viability of the culture. The desired pH may be maintained by the use of a buffer such as morpholinoethanesulfonic acid (MES), morpholino-propanesulfonic acid (MOPS), and the like, or by choice of nutrient materials which inherently possess buffering properties, such as production media described herein.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form because less pure materials which contain traces of growth factors and considerable quantities of mineral nutrients are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Submerged aerobic cultural conditions are preferred for the production of compound (I) in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of compound (I). Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of compound (I) and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution. Temperature of the seed medium is maintained between 26° C. and 29° C., preferably 27° C.; culture growth will be inhibited below this range and culture death will occur above this range. Incubation of the seed medium is usually conducted for a period of about 24 to 72 hours, preferably 48 hours, on a rotary shaker operating at about 220 rpm; the length of incubation time may be varied according to fermentation conditions and scales. Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The preferred culturing/production media for carrying out the fermentation are the following media:

| Seed Medium A | |
|---|---|
| Component | g/L |
| Dextrose | 1.0 |
| Dextrin | 10.0 |
| Beef extract | 3.0 |
| Ardamine pH | 5.0 |
| NZ Amine Type E | 5.0 |
| $MgSO_4.7H_2O$ | 0.05 |
| $K_2HPO_4$ | 0.37 |
| Adjust pH to 7.1 | |
| Add $CaCO_3$ 0.5 g/L | |

| Transformation Medium B | |
|---|---|
| Component | g/L |
| Glucose | 10.0 |
| Hycase SF | 2.0 |
| Beef Extract | 1.0 |
| Corn Steep Liquor | 3.0 |
| Adjust pH to 7.0 | |

The product, compound (I), can be recovered from the culture medium by conventional means which are commonly used for the recovery of other known biologically active substances. Compound (I) is found in the cultured mycelium and filtrate, which are obtained by filtering or centrifuging the cultured broth, and accordingly can be isolated and purified from the mycelium and the filtrate by a conventional method such as concentration under reduced pressure, lyophilization, extraction with a conventional solvent, such as methylene chloride and the like, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization, and the like. A preferred recovery method is solvent extraction, particularly using methylene chloride. A preferred purification method involves the use of chromatography, especially HPLC, using a silica gel column and an eluant mixture composed of water and an organic solvent such as methanol, acetonitrile and the like, and a small amount of acid such as acetic acid, trifluoracetic acid, phosphoric acid and the like. A preferred eluant is composed of water containing 0.1% trifluoroacetic acid and acetonitrile and is run through the column in a linear gradient.

The product of this invention, compound (I), exhibits A II antagonist activity by the $IC_{50}$ assay, and therefore is useful in treating hypertension. Compound (I) is also of value in the management of acute and chronic congestive heart failure. This compound may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The products of this invention are also useful for cognitive function enhancement. The application of the compounds of this invention for these and similar disorders will be apparent to those skilled in the art.

The compound of this invention is also useful to treat elevated intraocular pressure and to enhance retinal blood flow and can be administered to patients in need of such treatment with typical pharmaceutical formulations such as tablets, capsules, injectables, as well as topical ocular formulations in the form of solutions, ointments, inserts, gels, and the like. Pharmaceutical formulations prepared to treat intraocular pressure would typically contain about 0.1 to 15% by weight, preferably 0.5% to 2% by weight, of the compounds of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compound of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Preferably, the dosage range will be about 2.5 to 250 mg per patient per day; more preferably about 2.5 to 75 mg per patient per day.

The compound of this invention can also be administered in combination with other antihypertensives such as α-methyldopa, and/or diuretics such as hydrochlorothiazide, and/or angiotensin converting enzyme inhibitors such as enalapril, and/or calcium channel blockers such as nifedipine. Typically, the individual daily dosages for these combinations can range from about one-fifth of the minimally recommended clinical dosages to the maximum recommended levels for the entities when they are given singly. These dose ranges can be adjusted on a unit basis as necessary to permit divided daily dosage and, and as noted above, the dose will vary depending on the nature and severity of the disease, weight of the patient, special diets and other factors. Typically, these combinations can be formulated into pharmaceutical compositions as discussed below.

About 1 to 100 mg of compound (I) or a physiologically acceptable salt thereof, or any combination of these compounds or their physiologically acceptable salt forms, is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

RECEPTOR BINDING ASSAY USING RABBIT AORTAE MEMBRANE PREPARATION

Three frozen rabbit aortae (obtained from Pel-Freeze Biologicals) were suspended in 5 mM Tris-0.25M Sucrose, pH 7.4 buffer (50 mL) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/mL Bacitratin and the suspension was used for 100 assay tubes. Samples tested for screening were done in duplicate. To the membrane preparation (0.25 mL)

there was added $^{125}$I-Sar$^1$Ile$^8$-angiotensin II [obtained from New England Nuclear] (10 uL; 20,000 cpm) with or without the test sample and the mixture was incubated at 37° C. for 90 minutes. The mixture was then diluted with ice-cold 50 mM Tris-0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Using the methodology described above, the compounds of this invention were evaluated and were found to exhibit an activity of at least IC$_{50}$<50 μm thereby demonstrating and confirming the utility of the compounds of this invention as effective AII antagonists.

The following example is given for the purpose of illustrating the present invention and should not be construed as being a limitation on the scope or spirit of the instant invention.

EXAMPLE 1

Microorganism and Culture Conditions

A frozen vial (approximately 2.0 mL) of Streptomyces sp. MA6966 (ATCC 55293) was used to inoculate a 250 mL baffled shake flask containing 50 mL of medium A. The seed flasks were incubated at 27° C. for 24 hours on a rotary shaker operating at 220 rpm. A 2.5 mL aliquot of the resulting seed culture was used to inoculate 250 mL non-baffled shake flasks; each flask contained 50 mL of previously autoclaved medium B, used as transformation medium. Substrate compound (II) was added as an aqueous solution with pH of 7 at 0 hour to achieve a final concentration of 0.1 mg/mL in each flask. The resulting flasks with their contents were subsequently incubated for 2 days at 27° C. on a rotary shaker operating at 220 rpm. The resultant broths were combined for isolation and purification.

Isolation and Purification

The whole broth was maintained at pH 7.0 and centrifuged. The mycelial cake was washed with water, then discarded. The clear filtrate and washings were pooled and passed thru a Spe-ed octadecyl cartridge (14% carbon load, Applied Separations, Lehigh Valley, Pa.) under vacuum. The column was washed with 10% aqueous methanol. Column effluent and wash did not contain microbial product when tested with HPLC. The cartridge was eluted with methanol. Methanol was evaporated to dryness under reduced pressure at 30° C. The resulting oil was dissolved in methanol and subjected to purification by HPLC. HPLC was carried out on Whatman Magnum 20 Partisil 10 ODS-3 Column (C18, 22.1 mm ID×25 cm) at room temperature and monitored at 250 nm. The column was developed at 6 mL/min with linear gradient from 15% to 80% acetonitrile in 0.1% aqueous phosphoric acid over 80 minuted. The metabolite fractions were pooled, adjusted to pH 3.0 and evaporated to remove acetonitrile. The desalting was carried out using a C$_{18}$ Sep-Pak (Waters Associates) and methanol-water elution solvent to yield pure compound (I).

Characterization

Compound (I) of this invention was identified via NMR spectroscopy yielding the following proton NMR spectrum:

$^1$H NMR (250 MHz, CD$_3$OD/TMS, ppm), 0.85 (3H, T, J=7.3 Hz), 1.35 (2H, m), 1.8 (2H, q, J=7.5 Hz), 4.48 (2H, s), 4.6 (1H, t, J=7.0 Hz), 5.5 (2H, s), 7.04 (2H, d, J=8.s Hz), 7.14 (2H, d, J=8.2 Hz), 7.55 (2H, m), 7.7 (2H, m).

The mass spectral characteristics are as follows: FAB-MS M/Z=439 (M+H).

What is claimed is:

1. A compound of structural formula (I):

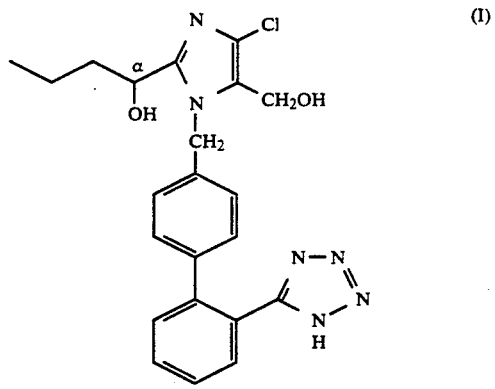

2. An antihypertensive pharmaceutical composition comprising a non-toxic therapeutically effective amount of the compound of claim 1 and a pharmaceutically acceptable carrier.

3. A method of treating hypertension or congestive heart failure comprising the administration of a non-toxic therapeutically effective amount of the compound of claim 1 to a subject in need of such treatment.

* * * * *